United States Patent
Manku et al.

(10) Patent No.: US 9,192,674 B2
(45) Date of Patent: *Nov. 24, 2015

(54) COSMETIC COMPOSITIONS COMPRISING EPA AND GLA AND METHODS OF MAKING AND USING SAME

(71) Applicant: Dignity Sciences Limited, Leopardstown, Dublin (IE)

(72) Inventors: Mehar Manku, Birmingham (GB); John Climax, Leopardstown (IE); David Coughlan, Leopardstown (IE)

(73) Assignee: Dignity Sciences Limited, Dublin (IE)

(*) Notice: Subject to any disclaimer, the term of this patent is extended or adjusted under 35 U.S.C. 154(b) by 31 days.

This patent is subject to a terminal disclaimer.

(21) Appl. No.: 14/020,176

(22) Filed: Sep. 6, 2013

(65) Prior Publication Data

US 2014/0066509 A1    Mar. 6, 2014

Related U.S. Application Data

(60) Provisional application No. 61/697,631, filed on Sep. 6, 2012.

(51) Int. Cl.
| | |
|---|---|
| *A61K 8/36* | (2006.01) |
| *A61Q 19/08* | (2006.01) |
| *A61K 47/12* | (2006.01) |
| *A61K 8/368* | (2006.01) |
| *A61Q 19/00* | (2006.01) |
| *A61K 31/202* | (2006.01) |
| *A61K 31/375* | (2006.01) |
| *A61K 31/60* | (2006.01) |

(52) U.S. Cl.
CPC ............. *A61K 47/12* (2013.01); *A61K 8/361* (2013.01); *A61K 8/368* (2013.01); *A61K 31/202* (2013.01); *A61K 31/375* (2013.01); *A61K 31/60* (2013.01); *A61Q 19/00* (2013.01); *A61Q 19/004* (2013.01); *A61Q 19/08* (2013.01)

(58) Field of Classification Search
CPC ....... A61Q 19/08; A61Q 19/00; A61K 8/361; A61K 47/12; A61K 31/60; A61K 31/375; A61K 31/202; A61K 8/368; A61K 2300/00
See application file for complete search history.

(56) References Cited

U.S. PATENT DOCUMENTS

| | | | |
|---|---|---|---|
| 5,312,834 A | 5/1994 | Yeo | |
| 5,409,955 A | 4/1995 | Bockow et al. | |
| 2002/0198177 A1* | 12/2002 | Horrobin | 514/78 |
| 2006/0257352 A1* | 11/2006 | Saar | 424/74 |
| 2007/0105954 A1* | 5/2007 | Puri | 514/529 |

OTHER PUBLICATIONS

Chen, Yung-Chih et al.; "Therapeutic Effect of Topical Gamma-Linolenic Acid on Refractory Uremic Pruritus"; American Journal of Kidney Diseases, vol. 48, No. 1, Jul. 2006, pp. 69-76.
Desbois, A. P. et al.; "Antibacterial free fatty acids: activities, mechanisms of action and biotechnological potential" Appl Microbiol Biotechnol, (2010) vol. 85 pp. 1629-1642.
Dewsbury, E. et al.; "Topical eicosapentaenoic acid (EPA) in the treatment of psoriasis" British Journal of Dematology (1989) 120, pp. 518-584.
Horrobin D. F.; "Nutritonal and Medical Importance of Gamma-Linolenic Acid"; Prog. lipid Res. vol. 31, No. 2. pp. 163-194, 1992.
Kanehara, S. et al.; "Undershirts coated with borage oil alleviate the symptoms of atopic dermatitis in children" ; EJD, vol. 17, No. 5, Sep.-Oct. 2007, 2 pages.
Kawamura, A. et al.; "Dietary Supplemental of Gamma-Linolenic Acid Improves Skin Parameters in Subjects with Dry Skin and Atopic Dermatitis"; Journal of oleo Science; vol. 60, No. 12, pp. 597-607, 2011.
Miller, C. C. et al.; Induction of Epidermal Hyperproliferation by Topical n-3 Ployunsaturated Fatty Acids on Guinea Pig Skin Linked to Decreased Levels of 13-Hydroxyoctadecadienoic Acid (13-Hode); The Journal of Investigative Dermatology, vol. 94, No. 3, Mar. 1990, 7 pages.
Stillman, M. A. et al.; "Relative irritancy of free fatty acids of different chain length"; Contact Dermatitis, 1975, 1, pp. 65-69.
Thiboutot, et al.; New insights into the management of ance: An update from Global Alliance to Improve Outcomes in Acne Group; J Am Acad Dermatol, May 2009, vol. 60, No. 5, 50 pages.
Uchida, A. et al.; "Antibacterial and Antialgal Substances Produced by the Dinoflagellate Peridinium bipes"; Nippon Sisan Gakkaishi : Formerly Bull. japan. Soc. Sci. Fish., vol. 54, No. 11, (1998), pp. 1941-1945.
Watanabe, T. et al.; "The effect of a newly developed ointment containing eicosapentaenoic acid and docosahexaenoic acid in the treatment of atopic dermatitis" ; The Journal of Medicine Investigation; vol. 46, 1999, 5 pages.
Zulfakar, M. H. et al.; "Is there a role for topically delivered eicosapentaenoic acid in the treatment of psoriasis"; Eur J Dermatol, 2007, vol. 17, No. 4, pp. 284-291.

\* cited by examiner

*Primary Examiner* — Anoop Singh
*Assistant Examiner* — Doan Phan
(74) *Attorney, Agent, or Firm* — Perkins Coie LLP

(57) ABSTRACT

The present disclosure is directed generally to cosmetic compositions comprising EPA free acid and GLA free acid. In some embodiments, the cosmetic compositions have a cosmetically acceptable odor.

19 Claims, No Drawings

US 9,192,674 B2

COSMETIC COMPOSITIONS COMPRISING EPA AND GLA AND METHODS OF MAKING AND USING SAME

CROSS REFERENCE TO RELATED APPLICATIONS

This application claims the benefit of U.S. Provisional Application Ser. No. 61/697,631, filed Sep. 6, 2012, the disclosure of which is hereby incorporated by reference in its entirety.

FIELD

The disclosure generally relates to cosmetic compositions comprising eicosapentaenoic free acid and gamma-linolenic free acid, and methods of manufacture and use thereof.

BACKGROUND

Compositions which include free fatty acid components—including those for topical and/or cosmetic use are well-known to develop unpleasant odors. It is believed that decomposition (e.g., oxidation) of the free fatty acid component(s) is the source of the odor. One strategy to avoid odor formation has been to use derivatives of the fatty acids, for example esters, triglycerides, etc. However, preparing derivatives of free fatty acids from source materials is time-consuming, costly, and in some cases attenuates the desired activity of the compounds. On the other hand, offensive odors in personal care products contributes to non-compliance with a recommended treatment schedule. In addition, derivatives of free fatty acids such as alkyl esters are generally much less soluble in aqueous compositions. Especially for cosmetic compositions, then, the decreased hydrophilicity of fatty acid derivatives is undesirable as organic co-solvents tend to be harsher on the skin than water-based compositions. Accordingly, there exists a need for compositions comprising free fatty acids without an associated unpleasant odor.

SUMMARY

The present disclosure provides compositions comprising free fatty acid agents including, for example, eicosapentaenoic free acid and gamma-linolenic free acid. In some embodiments, the eicosapentaenoic free acid and the gamma-linolenic free acid are present in a weight ratio of about 2:1 to about 8:1, for example about 4:1. In some embodiments, the eicosapentaenoic free acid is present in an amount of about 0.5 wt. % to about 8 wt. %, about 0.8 wt. % to about 4 wt. %, about 0.815 wt. %, about 1.631 wt. %, or about 4.080 wt. %. In some embodiments, the gamma-linolenic free acid is present in an amount of about 0.1 wt. % to about 3 wt. %, about 0.2 wt. % to about 1.5 wt. %, about 0.285 wt. %, about 0.570 wt. %, or about 1.425 wt. %. In some embodiments, the compositions further comprise one or more excipients. Such compositions are free of unpleasant odors typically associated with compositions comprising free fatty acids and thus are useful as topical, cosmetic and/or personal care products.

In some embodiments, the composition further comprises one or more excipients selected from the group consisting of: solvents, sequestrants, humectants, thickening agents, emulsifiers, emollients, adsorbing agents, preservatives, fragrances, antioxidants, pH modifiers, texturizing agents, and combinations thereof. In some embodiments, the excipients comprise: water, Glycerine Veg. PH EUR 99.5% (Glycerin), Trilon B (Disodium EDTA), Cosmedia SP (sodium polyacrylate), Lincol BAS (C12-15 alkyl benzoate), Lincol SN (cetearyl isononanoate), Burro Di KARITE (butyrospermum parkii butter), Euxyl PE 9010 (phenoxyethanol & ethylhexylglycerin), Profumo Fiori D'acqua 85328, Lipochroman (dimethylmethoxy chromanol), Ascorbyl palmitate, Imwitor 372P (glyceryl stearate citrate), Cutina GMS/Bergabest GS40/Lincol GMS (glyceryl stearate), Lanette 22/Vegarol 22/Akest AB/Nafol 1822C (behenyl alcohol), Sodium hydroxide and Dry-Flo PC (aluminum starch octenylsuccinate). In some embodiments, the excipients comprise: water, Trilon B (Disodium EDTA), Glycerine Veg. PH EUR 99.5% (Glycerin), Silwax WS (PEG-8-dimethicone), Gransil EPS (polysilicone-11 & laureth 12), Velvesil DM (dimethicone & detearyl dimethicone crosspolymer), Cosmedia Silc (silica), Granpowder USQ (polyurethane and polymethylsilsesquioxane), Cosmedia SP (sodium polyacrylate), Cetiol Sensoft (propylheptyl caprylate), Euxyl PE 9010 (phenoxyethanol & ethylhexylglycerin), Profumo Fiori D'acqua 85328 and Lipochroman (dimethylmethoxy chromanol). In some embodiments, the excipients comprise: water, Trilon B (Disodium EDTA), Glycerine Veg. PH EUR 99.5% (Glycerin), Silwax WS (PEG-8-dimethicone), Gransil EPS (polysilicone-11 & laureth 12), Velvesil DM (dimethicone & detearyl dimethicone crosspolymer), Cosmedia Silc (silica), Aristoflex AVC (polymeric sulphonic acid), Cetiol Sensoft (propylheptyl caprylate), Euxyl PE 9010 (phenoxyethanol & ethylhexylglycerin), Profumo Fiori D'acqua 85328 and Aperoxide TLA (tocopherol, lecithin, ascorbyl palmitate and citric acid).

The present disclosure also provides methods for treating and/or preventing a condition (e.g., a skin condition such as wrinkles, sunburn, seborrheic dermatitis, etc.) in a subject in need thereof comprising administering to a subject a composition comprising a therapeutically effective amount of eicosapentaenoic free acid and gamma-linolenic free acid.

In some embodiments, the compositions are formulated for topical administration, such as a cream, an ointment, an oil, a liniment, a powder, an aerosol, a shampoo, or any other form reasonably adapted for topical administration.

These and other embodiments of the invention are described in further detail below.

DETAILED DESCRIPTION

The present disclosure provides compositions (e.g., cosmetic compositions) and formulations that comprise fatty acid agents including, for example, eicosapentaenoic free acid and gamma-linolenic free acid, said compositions free of unpleasant odors commonly associated with free fatty acid compounds. Such agents have been found to positively affect (e.g., treat and/or prevent) skin conditions such as wrinkles, UV damage and seborrheic dermatitis. Given this capacity, the compositions and formulations disclosed herein may be used in the treatment and/or prevention of skin conditions.

While the present disclosure is capable of being embodied in various forms, the description below of several embodiments is made with the understanding that the present disclosure is to be considered as an exemplification of the disclosure, and is not intended to limit the disclosure to the specific embodiments illustrated. Headings are provided for convenience only and are not to be construed to limit the disclosure in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios)

that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

Eicosapentaenoic acid, an omega-3 fatty acid also known as all-cis-5,8,11,14,17-eicosapentaenoic acid or (5Z,8Z,11Z,14Z,17Z)-5,8,11,14,17-icosapentaenoic acid, is typically derived from fish oil and/or algae. As used herein, the term "EPA" refers to eicosapentaenoic acid in its free acid form unless otherwise expressly stated. In some embodiments of the present disclosure, EPA is provided in a composition comprising at least about 95% by weight EPA, for example at least about 95% by weight EPA, at least about 96% by weight EPA, at least about 97% by weight EPA, at least about 98% by weight EPA, at least about 98.1% by weight EPA, or at least about 99% by weight EPA.

Gamma-linolenic acid, an omega-6 fatty acid also known as γ-linolenic acid, gamolenic acid, all-cis-6,9,12-octadecatrienoic acid, is generally derived from vegetable oils and seed oils. As used herein, the term "GLA" refers to gamma-linolenic acid in its free acid form unless otherwise expressly stated. In some embodiments of the present disclosure, GLA is provided in a composition comprising at least about 70% by weight GLA, for example at least about 70% by weight GLA, at least about 70.2% by weight GLA, at least about 71% by weight GLA, at least about 72% by weight GLA, at least about 73% by weight GLA, at least about 74% by weight GLA, at least about 75% by weight GLA, at least about 76% by weight GLA, at least about 77% by weight GLA, at least about 78% by weight GLA, at least about 79% by weight GLA, at least about 80% by weight GLA, at least about 81% by weight GLA, at least about 82% by weight GLA, at least about 83% by weight GLA, at least about 84% by weight GLA, at least about 85% by weight GLA, at least about 86% by weight GLA, at least about 87% by weight GLA, at least about 88% by weight GLA, or at least about 89% by weight GLA. In some embodiments, the GLA is provided as an oil comprising: about 70% GLA, about 5.5% Palmitic acid (16:0), about 3.6% Stearic acid, about 3.4% Oleic acid, about 13.1% Linoleic acid, about 1.6% Icosenoic acid, and about 1.8% Docosenoic acid.

As used herein, the term "animal" means any animal that has a need for preventing or treating arthritis and maintaining joint health in an animal, including human, avian, bovine, canine, equine, feline, lupine, murine, ovine, or porcine animals.

As used herein, the term "therapeutically effective amount" means an amount of a compound of the invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

As used herein, the terms "treating", "treat", and "treatment" embrace both preventative, i.e., prophylactic, and palliative treatment.

As used herein, the term "cosmetic composition" means a composition that is formulated for use as a cosmetic, or a formulation that is not specifically formulated for use as a cosmetic but could reasonably be used as a cosmetic without further modification.

As used herein, the terms "free of unpleasant odor" and "cosmetically acceptable odor" are used interchangeably and mean generally that a majority or large majority of subjects rate or would rate the composition as having no fish odor or low fish odor.

In some embodiments, the EPA is present in an amount of about 0.4 wt. % to about 8 wt. %, for example about 0.4 wt. %, about 0.5 wt. %, about 0.815 wt. %, about 1 wt. %, about 1.5 wt. %, about 1.631 wt. %, about 2 wt. %, about 2.5 wt. %, about 3 wt. %, about 3.5 wt. %, about 4 wt. %, about 4.5 wt. %, about 5 wt. %, about 5.5 wt. %, about 6 wt. %, about 6.5 wt. %, about 7 wt. %, about 7.5 wt. %, or about 8 wt. %. The term "the EPA is present in an amount" refers herein to the amount of EPA free acid in the composition. For example, in embodiments wherein the EPA is provided as an EPA composition comprising 98.1 wt. % EPA, the EPA composition is added to the cosmetic composition in an amount sufficient to provide EPA in an amount of about 0.5 wt. % to about 8 wt. %, taking into account the actual amount of EPA in the EPA composition. In some embodiments, the EPA is present in an amount of about 0.8 wt. % to about 4 wt. %, for example about 0.8 wt. %, about 0.815 wt. %, about 1 wt. %, about 1.25 wt. %, about 1.5 wt. %, about 1.631 wt. %, about 1.75 wt. %, about 2 wt. %, about 2.25 wt. %, about 2.5 wt. %, about 2.75 wt. %, about 3 wt. %, about 3.25 wt. %, about 3.5 wt. %, about 3.75 wt. %, or about 4 wt. %. In some embodiments, the EPA is present in an amount of about 0.815 wt. %. In some embodiments, the EPA is present in an amount of about 1.631 wt. %. In some embodiments, the EPA is present in an amount of about 4.080 wt. %.

In some embodiments, the GLA is present in an amount of about 0.1 wt. % to about 3 wt. %, for example about 0.1 wt. %, about 0.25 wt. %, about 0.285 wt. %, about 0.5 wt. %, about 0.570 wt. %, about 0.75 wt. %, about 1 wt. %, about 1.25 wt. %, about 1.425 wt. %, about 1.5 wt. %, about 1.75 wt. %, about 2 wt. %, about 2.25 wt. %, about 2.5 wt. %, about 2.75 wt. %, about 3 wt. %. The term "the GLA is present in an amount" refers herein to the amount of GLA free acid in the composition. For example, in embodiments wherein the GLA is provided as a GLA composition comprising 70.2 wt. % GLA, the GLA composition is added to the cosmetic composition in an amount sufficient to provide GLA in an amount of about 0.1 wt. % to about 3 wt. %, taking into account the actual amount of GLA in the GLA composition. In some embodiments, the GLA is present in an amount of about 0.2 wt. % to about 1.5 wt. %, for example about 0.2 wt. %, about 0.25 wt. %, about 0.285 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 1 wt. %, about 1.05 wt. %, about 1.1 wt. %, about 1.15 wt. %, about 1.2 wt. %, about 1.25 wt. %, about 1.3 wt. %, about 1.35 wt. %, about 1.4 wt. %, about 1.45 wt. %, or about 1.5 wt. %. In some embodiments, the GLA is present in an amount of about 0.285 wt. %. In some embodiments, the GLA is present in an amount of about 0.570 wt. %. In some embodiments, the GLA is present in an amount of about 1.425 wt. %.

In some embodiments the GLA is provided as a GLA oil comprising about 70% GLA, by weight, and one or more of Palmitic acid, Stearic acid, Oleic acid, Linoleic acid, Icosenoic acid, and Docosenoic acid, wherein the GLA oil is added to the cosmetic composition in an amount sufficient to provide GLA in an amount of about 0.1 wt. % to about 3 wt. %, taking into account the actual amount of GLA in the GLA composition. In some embodiments, the GLA is present in an amount of about 0.2 wt. % to about 1.5 wt. %, for example about 0.2 wt. %, about 0.25 wt. %, about 0.285 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 1 wt. %, about 1.05 wt. %, about 1.1 wt. %, about 1.15 wt. %, about 1.2 wt. %, about 1.25 wt. %, about 1.3 wt. %, about 1.35 wt. %, about 1.4 wt. %, about 1.45 wt. %, or about 1.5 wt. %. In some embodiments, the GLA is present in an amount of about 0.285 wt. %. In some embodiments, the GLA is present in an amount of about 0.570 wt. %. In some embodiments, the GLA is present in an amount of about 1.425 wt. %.

In some embodiments the GLA is provided as a GLA oil comprising about 70 wt. % GLA, about 5.5 wt. % Palmitic acid, about 3.6 wt. % Stearic acid, about 3.4 wt. % Oleic acid, about 13.1 wt. % Linoleic acid, about 1.6 wt. % Icosenoic acid, and about 1.8 wt. % Docosenoic acid, wherein the GLA oil is added to the cosmetic composition in an amount sufficient to provide GLA in an amount of about 0.1 wt. % to about 3 wt. %, taking into account the actual amount of GLA in the GLA composition. In some embodiments, the GLA is present in an amount of about 0.2 wt. % to about 1.5 wt. %, for example about 0.2 wt. %, about 0.25 wt. %, about 0.285 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 1 wt. %, about 1.05 wt. %, about 1.1 wt. %, about 1.15 wt. %, about 1.2 wt. %, about 1.25 wt. %, about 1.3 wt. %, about 1.35 wt. %, about 1.4 wt. %, about 1.45 wt. %, or about 1.5 wt. %. In some embodiments, the GLA is present in an amount of about 0.285 wt. %. In some embodiments, the GLA is present in an amount of about 0.570 wt. %. In some embodiments, the GLA is present in an amount of about 1.425 wt. %.

In one embodiment, a cosmetic composition according to the present disclosure comprises EPA, GLA and one or more excipients. In some embodiments, the EPA and GLA are present in amounts such that the weight ratio of EPA to GLA is about 2:1 to about 8:1, for example about 2:1, about 3:1, about 4:1, about 5:1, about 6:1, about 7:1, or about 8:1.

In some embodiments, the EPA and GLA are present in a weight ratio of about 4:1. Thus, in such embodiments, EPA is present in an amount of about 0.5 wt. % to about 8 wt. %, and GLA is present in an amount of about 0.125 wt. % to about 2 wt. %. Alternatively, GLA is present in such embodiments in an amount of about 0.1 wt. % to about 2 wt. %, and EPA is present in an amount of about 0.4 wt. % to about 8 wt. %.

In some embodiments, a cosmetic composition of the present disclosure comprises about 0.815 wt. % to 4.08 wt. % EPA, about 0.285 wt. % to about 1.425 wt. % GLA, and one or more cosmetically acceptable excipients. In some embodiments, the EPA and GLA are present in a weight ratio of about 4:1. In some embodiments, the excipients are selected from the group consisting of: solvents, sequestrants, humectants, thickening agents, emulsifiers, emollients, adsorbing agents, preservatives, fragrances, antioxidants, pH modifiers, texturizing agents, and combinations thereof.

Cosmetic compositions of the present disclosure further comprise a solvent. In some embodiments, the solvent comprises water. In some embodiments, the solvent comprises water. In embodiments of the present disclosure, the solvent is present in an amount of about 50 wt. % to about 85 wt. %, for example about 50 wt. %, about 51 wt. %, about 52 wt. %, about 53 wt. %, about 54 wt. %, about 55 wt. %, about 56 wt. %, about 57 wt. %, about 58 wt. %, about 59 wt. %, about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. %, about 78 wt. %, about 79 wt. %, about 80 wt. %, about 81 wt. %, about 82 wt. %, about 83 wt. %, about 84 wt. %, or about 85 wt. %. In some embodiments, the solvent is present in an amount of about 76.685 wt. %. In some embodiments, the solvent is present in an amount of about 80.289 wt. %. In some embodiments, the solvent is present in an amount of about 81.59 wt. %. In some embodiments, the solvent is present in an amount of about 77.645 wt. %. In some embodiments, the solvent is present in an amount of about 81.249 wt. %. In some embodiments, the solvent is present in an amount of about 82.55 wt. %. In some embodiments, the solvent is present in an amount of about 72.875 wt. %. In some embodiments, the solvent is present in an amount of about 76.179 wt. %. In some embodiments, the solvent is present in an amount of about 77.28 wt. %.

In some embodiments, a cosmetic composition of the present disclosure further comprises a sequestrant. Any sequestrant suitable for use in a cosmetic composition is contemplated. In some embodiments, the sequestrant is one or more of tetrasodium EDTA (TRILON B), disodium EDTA (TRILON B), calcium disodium EDTA, glucono delta-lactone, sodium gluconate, potassium gluconate, sodium tripolyphosphate, sodium hexametaphosphate, and combinations thereof. In some embodiments, the sequestrant is tetrasodium EDTA. In some embodiments, the sequestrant is disodium EDTA. In some embodiments, the sequestrant is present in an amount of about 0.01 wt. % to about 0.5 wt. %, for example about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.20 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, about 0.30 wt. %, about 0.31 wt. %, about 0.32 wt. %, about 0.33 wt. %, about 0.34 wt. %, about 0.35 wt. %, about 0.36 wt. %, about 0.37 wt. %, about 0.38 wt. %, about 0.39 wt. %, about 0.40 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, or about 0.5 wt. %. In some embodiments, the sequestrant is present in an amount of about 0.10 wt. %.

In some embodiments, a cosmetic composition of the present disclosure further comprises a humectant. Any humectant suitable for use in a cosmetic composition is contemplated. In some embodiments, the humectant is one or more of propylene glycol, glyceryl triacetate, vinyl alcohol, neoagarobiose, a sugar polyol, a polymeric polyol, quillaia, lactic acid, urea, glycerine, aloe vera gel, MP Diol, an alpha-hydroxy acid, honey, and combinations thereof. In some embodiments, the humectant is a glycerine, such as Glycerine Veg. PH EUR. In some embodiments, the humectant is present in an amount of about 0.5 wt. % to about 5 wt. %, for example about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. %. In some embodiments, the humectant is present in an amount of about 3 wt. %.

In some embodiments, a cosmetic composition of the present disclosure further comprises a texturizing agent. Any texturizing agent suitable for use in a cosmetic composition is contemplated. In some embodiments, the texturizing agent is one or more of PEG-8-dimethicone (SILWAX WS), polysilicone-11, laureth-12, a crosspolymer of dimethicone and detearyl dimethicone (VELVESIL DM), silica (COSMEDIA SILC), polyurethane, polymethylsilsesquioxane, a mixture of polysilicone-11 and laureth-12 (GRANSIL EPS), a mixture of polyurethane and polymethylsilsesquioxane (GRANPOWDER USQ), and combinations thereof. In some embodiments, the texturizing agent is a combination of SIL-WAX WS, GRANSIL EPS, VELVESIL DM, COSMEDIA SILC, and GRANPOWDER USQ. In some embodiments, the cosmetic composition does not include a texturizing agent. In some embodiments, the texturizing agent is present in an amount of about 0.5 wt. % to about 15 wt. %, for example about 0.5 wt. %, about 0.75 wt. %, about 1 wt. %, about 1.25 wt. %, about 1.5 wt. %, about 1.75 wt. %, about 2 wt. %, about 2.25 wt. %, about 2.5 wt. %, about 2.75 wt. %, about 3 wt. %, about 3.25 wt. %, about 3.5 wt. %, about 3.75 wt. %, about 4 wt. %, about 4.25 wt. %, about 4.5 wt. %, about 4.75 wt. %, about 5 wt. %, about 5.25 wt. %, about 5.5 wt. %, about 5.75 wt. %, about 6 wt. %, about 6.25 wt. %, about 6.5 wt. %, about 6.75 wt. %, about 7 wt. %, about 7.25 wt. %, about 7.5 wt. %, about 7.75 wt. %, about 8 wt. %, about 8.25 wt. %, about 8.5 wt. %, about 8.75 wt. %, about 9 wt. %, about 9.25 wt. %, about 9.5 wt. %, about 9.75 wt. %, about 10 wt. %, about 10.25 wt. %, about 10.5 wt. %, about 10.75 wt. %, about 11 wt. %, about 11.25 wt. %, about 11.5 wt. %, about 11.75 wt. %, about 12 wt. %, about 12.25 wt. %, about 12.5 wt. %, about 12.75 wt. %, about 13 wt. %, about 13.25 wt. %, about 13.5 wt. %, about 13.75 wt. %, about 14 wt. %, about 14.25 wt. %, about 14.5 wt. %, about 14.75 wt. %, or about 15 wt. %. In some embodiments, the texturizing agent is present in an amount of about 8 wt. %. In some embodiments, the texturizing agent is present in an amount of about 9 wt. %.

In some embodiments, a cosmetic composition of the present disclosure further comprises a thickening agent. Any thickening agent suitable for use in a cosmetic composition is contemplated. In some embodiments, the thickening agent is one or more of sodium polyacrylate (COSMEDIA SP), polymeric sulphonic acid (ARISTOFLEX AVC), or combinations thereof. In some embodiments, the thickening agent is sodium polyacrylate (COSMEDIA SP). In some embodiments, the thickening agent is polymeric sulphonic acid (ARISTOFLEX AVC). In some embodiments, the thickening agent is present in an amount of about 0.1 wt. % to about 5 wt. %, for example about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. %. In some embodiments, the thickening agent is present in an amount of about 0.5 wt. %. In some embodiments, the thickening agent is present in an amount of about 1 wt. %.

In some embodiments, a cosmetic composition of the present disclosure further comprises an emollient. Any emollient suitable for use in a cosmetic composition is contemplated. In some embodiments, the emollient is one or more of propylheptyl caprylate (CETIOL SENSOFT), C12-15 alkyl benzoate (LINCOL BAS), cetearyl isononanoate (LINCOL SN), butyrospermum parkii butter (BURRO DI KARITE), and combinations thereof. In some embodiments, the emollient is propylheptyl caprylate (CETIOL SENSOFT). In some embodiments, the emollient is a mixture of C12-15 alkyl benzoate (LINCOL BAS), cetearyl isononanoate (LINCOL SN) and butyrospermum parkii butter (BURRO DI KARITE). In some embodiments, the emollient is present in an amount of about 1 wt. % to about 20 wt. %, for example about 1 wt. %, about 1.25 wt. %, about 1.5 wt. %, about 1.75 wt. %, about 2 wt. %, about 2.25 wt. %, about 2.5 wt. %, about 2.75 wt. %, about 3 wt. %, about 3.25 wt. %, about 3.5 wt. %, about 3.75 wt. %, about 4 wt. %, about 4.25 wt. %, about 4.5 wt. %, about 4.75 wt. %, about 5 wt. %, about 5.25 wt. %, about 5.5 wt. %, about 5.75 wt. %, about 6 wt. %, about 6.25 wt. %, about 6.5 wt. %, about 6.75 wt. %, about 7 wt. %, about 7.25 wt. %, about 7.5 wt. %, about 7.75 wt. %, about 8 wt. %, about 8.25 wt. %, about 8.5 wt. %, about 8.75 wt. %, about 9 wt. %, about 9.25 wt. %, about 9.5 wt. %, about 9.75 wt. %, about 10 wt. %, about 10.25 wt. %, about 10.5 wt. %, about 10.75 wt. %, about 11 wt. %, about 11.25 wt. %, about 11.5 wt. %, about 11.75 wt. %, about 12 wt. %, about 12.25 wt. %, about 12.5 wt. %, about 12.75 wt. %, about 13 wt. %, about 13.25 wt. %, about 13.5 wt. %, about 13.75 wt. %, about 14 wt. %, about 14.25 wt. %, about 14.5 wt. %, about 14.75 wt. %, about 15 wt. %, about 15.25 wt. %, about 15.5 wt. %, about 15.75 wt. %, about 16 wt. %, about 16.25 wt. %, about 16.5 wt. %, about 16.75 wt. %, about 17 wt. %, about 17.25 wt. %, about 17.5 wt. %, about 17.75 wt. %, about 18 wt. %, about 18.25 wt. %, about 18.5 wt. %, about 18.75 wt. %, about 19 wt. %, about 19.25 wt. %, about 19.5 wt. %, about 19.75 wt. %, or about 20 wt. %. In some embodiments, the emollient is present in an amount of about 3 wt. %. In some embodiments, the emollient is present in an amount of about 10 wt. %.

In some embodiments, a cosmetic composition of the present disclosure further comprises a preservative. Any preservative suitable for use in a cosmetic composition is contemplated. In some embodiments, the preservative is one or more of benzoic acid, proprionic acid, salicylic acid, sorbic acid, biphenyl-2-ol, 4-hydroxybenzoic acid, 3-acetyl-6-methylpyran-2,4-(3H)-dione, formic acid, 3-3'-dibromo-4,4'-hexamethyulene-dioxydibenzamidineundec-10-enoic acid, 1,6-di-(4-amidinophenoxy)-n-hexane, cosmetically acceptable salts and/or esters of the foregoing, phenoxyethanol, ethylhexylglycerine, a mixture of phenoxyethanol and ethylhexylglycerine (EUXYL PE 9010), zinc pyrithione, inorganic sulphites, hydrogensulphites, chlorobutanol, thiomersal, phenylmercuric salts, hexetidine, 5-bromo-5-nitro-1,3-dioxane, bronopol, 2,4-dichlorobenzyl alcohol, triclocarban, 4-chloro-m-cresol, triclosan, 4-chloro-3,5-xylenol, 3,3'-bis-(1-hydroxymethyl-2,5-dioxoimidazolidin-4-yl)-1,1'-methylenediurea (also referred to as imidazolidinyl urea), poly-(1-hexamethylenebiguanide hydrochloride), 2-phenoxyethanol, hexamethylenetetramine(methenamine), methenamine 3-chloroallylochloride, 1-(4-chlorophenoxy)-1-(imidazol-1-yl)-3,3-dimethylbutan-2-one, 1,3-bis(hydroxymethyl)-5,5-dimethylimidazoline-2,4-dione, benzyl alcohol, 1-hydroxy-4-methyl-6-(2,4,4-trimethylpentyl)-2-pyridon, monoethanolamine salt of 1-hydroxy-4-methyl-6-(2,4,4-trimethylpentyl)-2-pyridon, 6,6-dibromo-4,4-dichloro-2,2'-methylenediphenol:bromochlorophen, 4-isopropyl-m-cresol, a mixture of 5-chloro-2-methylisothiazol-3-(2H)-one and 2-methylisothizaol-3-(2H)-one with magnesium chloride and magnesium nitrate, 2-benzyl-4-chlorophenol (also referred to as chlorphene), chlorhexidine and its digluconate, diacetate and dihydrochloride, 1-phenoxypropan-2-ol, alkyl (C12-22) trimethyl ammonium bromide and chloride, 4,4-dimethyl-1,3-oxazolidine, N-(hydroxymethyl)-N-(dihydroxymethyl-1,3-dioxo-2,5-imidazolinidyl-4)-N'-(hydroxymethyl)urea, glutaraldehyde, 5-ehtyl-3,7-dioxa-1-azabicyclo[3.3.0]octane, 3-(p-chlorophenoxy)-propane-1,2-diol (also referred to as chlorphenesin), sodium hydroxymethylamino acetate, silver chloride deposited on titanium dioxide, benzethionium chloride, benzalkonium chloride, benzalkonium bromide, benzalkonium saccharinate, benzylhemiformal, iodopropynyl butyl-carbamate, methylisothiazolidinone, and combinations thereof. In some embodiments, the preservative is a mixture of phenoxyethanol and ethylhexylglycerine (EUXYL PE 9010). In some embodiments, the preservative is present in an amount of about 0.1 wt. % to about 5 wt. %, for example about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. %. In some embodiments, the thickening agent is present in an amount of about 0.5 wt. %. In some embodiments, the preservative is present in an amount of about 1 wt. %.

In some embodiments, a cosmetic composition of the present disclosure further comprises a fragrance. Any fragrance suitable for use in a cosmetic composition is contemplated. In some embodiments, the fragrance is PROFUMO FIORI D'ACQUA 85328. In some embodiments, the fragrance is present in an amount of about 0.05 wt. % to about 2 wt. %, for example about 0.05 wt. %, about 0.1 wt. %, about 0.15 wt. %, about 0.2 wt. %, about 0.25 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, or about 2 wt. %. In some embodiments, the fragrance is present in an amount of about 0.2 wt. %. In some embodiments, the fragrance is present in an amount of about 0.5 wt. %. In some embodiments, the fragrance is present in an amount of about 0.7 wt. %.

In some embodiments, a cosmetic composition of the present disclosure further comprises an antioxidant. Any antioxidant suitable for use in a cosmetic composition is contemplated. In some embodiments, the antioxidant is one or more of dimethylmethoxy chromanol (LIPOCHROMAN); tocopherol; lecithin; ascorbyl palmitate; citric acid; a mixture of tocopherol, lecithin, ascorbyl palmitate, citric acid (APEROXIDE TLA); idebenone; and combinations thereof. In some embodiments, the antioxidant is dimethylmethoxy chromanol (LIPOCHROMAN). In some embodiments, the antioxidant is a mixture of dimethylmethoxy chromanol (LIPOCHROMAN) and ascorbyl palmitate. In some embodiments, the antioxidant is a mixture of tocopherol, lecithin, ascorbyl palmitate, citric acid (APEROXIDE TLA). In some embodiments, the antioxidant is present in an amount of about 0.005 wt. % to about 0.1 wt. %, for example about 0.005 wt. %, about 0.01 wt. %, about 0.015 wt. %, about 0.02 wt. %, about 0.025 wt. %, about 0.03 wt. %, about 0.035 wt. %, about 0.04 wt. %, about 0.045 wt. %, about 0.05 wt. %, about 0.055 wt. %, about 0.06 wt. %, about 0.065 wt. %, about 0.07 wt. %, about 0.075 wt. %, about 0.08 wt. %, about 0.085 wt. %, about 0.09 wt. %, about 0.095 wt. %, or about 0.1 wt. %. In some embodiments, the antioxidant is present in an amount of about 0.01 wt. %. In some embodiments, the antioxidant is present in an amount of about 0.02 wt. %. In some embodiments, the antioxidant is present in an amount of about 0.05 wt. %.

In some embodiments, a cosmetic composition of the present disclosure further comprises an emulsifier. Any emulsifier suitable for use in a cosmetic composition is contemplated. In some embodiments, the emulsifier is one or more of glyceryl stearate citrate (IMWITOR 372P), glyceryl stearate (CUTINA GMS/BERGABEST GS40/LINCOL GMS), behenyl alcohol (LANETTE 22/VEGARAL 22/AKEST AB/NAFOL 1822C), and combinations thereof. In some embodiments, the emulsifier is a mixture of glyceryl stearate citrate (IMWITOR 372P), glyceryl stearate (CUTINA GMS/BERGABEST GS40/LINCOL GMS), and behenyl alcohol (LANETTE 22/VEGARAL 22/AKEST AB/NAFOL 1822C). In some embodiments, the cosmetic composition does not include an emulsifier. In some embodiments, the emulsifier is present in an amount of about 0.5 wt. % to about 10 wt. %, for example about 0.5 wt. %, about 0.75 wt. %, about 1 wt. %, about 1.25 wt. %, about 1.5 wt. %, about 1.75 wt. %, about 2 wt. %, about 2.25 wt. %, about 2.5 wt. %, about 2.75 wt. %, about 3 wt. %, about 3.25 wt. %, about 3.5 wt. %, about 3.75 wt. %, about 4 wt. %, about 4.25 wt. %, about 4.5 wt. %, about 4.75 wt. %, about 5 wt. %, about 5.25 wt. %, about 5.5 wt. %, about 5.75 wt. %, about 6 wt. %, about 6.25 wt. %, about 6.5 wt. %, about 6.75 wt. %, about 7 wt. %, about 7.25 wt. %, about 7.5 wt. %, about 7.75 wt. %, about 8 wt. %, about 8.25 wt. %, about 8.5 wt. %, about 8.75 wt. %, about 9 wt. %, about 9.25 wt. %, about 9.5 wt. %, about 9.75 wt. %, or about 10 wt. %. In some embodiments, the emulsifier is present in an amount of about 5 wt. %.

In some embodiments, a cosmetic composition of the present disclosure further comprises a pH modifier. Any pH modifier suitable for use in a cosmetic composition is contemplated. In some embodiments, the pH modifier is sodium hydroxide. In some embodiments, the cosmetic composition does not include a pH modifier. In some embodiments, the pH modifier is present in an amount sufficient to bring the pH of the composition to about 5 to about 8, for example about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. In some embodiments the pH is about 7 to about 7.15, for example about 7, about 7.01, about 7.02, bout 7.03, about 7.04, about 7.05 about 7.06, about 7.07, about 7.08 about 7.09, about 7.10, about 7.11 about 7.12, about 7.13, about 7.14, or about 7.15. In some embodiments, the pH is about 5.2 to about 5.5, for example about 5.2, about 5.28, about 5.3, about 5.32, about 5.35, about 5.4, about 5.41, or about 5.5. In some embodiments, the pH is about 5.8 to about 5.9, for example about 5.80, about 5.81, about 5.82, about 5.83, about 5.84, about 5.85, about 5.86, about 5.87, about 5.88, about 5.89, or about 5.90. In some embodiments, the pH modifier is present in an amount of about 0.05 wt. % to about 1 wt. %, for example about 0.05 wt. %, about 0.1 wt. %, about 0.15 wt. %, about 0.2 wt. %, about 0.25 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, or about 1 wt. %. In some embodiments, the pH modifier is present in an amount of about 0.3 wt. %.

In some embodiments, a cosmetic composition of the present disclosure further comprises an adsorbing agent. Any adsorbing agent suitable for use in a cosmetic composition is contemplated. In some embodiments, the adsorbing agent is aluminum starch octenylsuccinate (DRY-FLO PC). In some embodiments, the cosmetic composition does not include an adsorbing agent. In some embodiments, the adsorbing agent is present in an amount of about 0.1 wt. % to about 5 wt. %, for example about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. %. In some embodiments, the adsorbing agent is present in an amount of about 1 wt. %.

In some embodiments, the cosmetic composition comprises or consists of: 0.815 wt. % to 4.080 wt. % of EPA, 0.285 wt. % to 1.425 wt. % of GLA, 0.1 wt. % of a sequestrant (e.g., disodium EDTA), 3 wt. % of a humectant (e.g., glycerine), 9 wt. % of a texturizing agent (e.g., a mixture of PEG-8-dimethicone, polysilicone-11, laureth-12, a crosspolymer of dimethicone and cetearyl dimethicone, silica, polyurethane and polymethylsilsesquioxane), 1 wt. % of a thickening agent (e.g., sodium polyacrylate), 3 wt. % of an emollient (e.g., propylheptyl caprylate), 1 wt. % of a preservative (e.g., phenoxyethanol and ethylhexylglycerine), fragrance (e.g., Profumo Fiori D'acqua) in an amount of 0.2 wt. %, 0.4 wt. % or 0.7 wt. %, 0.01 wt. % of an antioxidant (e.g., dimethylmethoxy chromanol), and balance solvent (e.g., water), wherein the EPA and GLA are present in a weight-to-weight ratio of about 4:1. In one such embodiment, the EPA and GLA are present in amounts of 0.815 wt. % and 0.285 wt. %, respectively, and the fragrance is present in an amount of 0.2 wt. %. In another such embodiment, the EPA and GLA are present in amounts of 1.631 wt. % and 0.57 wt. %, respectively, and the fragrance is present in an amount of 0.4 wt. %. In yet another such embodiment, the EPA and GLA are present in amounts of 4.08 wt. % and 1.425 wt. %, respectively, and the fragrance is present in an amount of 0.7 wt. %.

In some embodiments, the cosmetic composition comprises or consists of: 0.815 wt. % to 4.08 wt. % of EPA, 0.285 wt. % to 1.425 wt. % of GLA, 0.1 wt. % of a sequestrant (e.g., disodium EDTA), 3 wt. % of a humectant (e.g., glycerine), 8 wt. % of a texturizing agent (e.g., a mixture of PEG-8-dimethicone, polysilicone-11, laureth-12, a crosspolymer of dimethicone and cetearyl dimethicone, and silica), 1 wt. % of a thickening agent (e.g., polymeric sulphonic acid), 3 wt. % of an emollient (e.g., propylheptyl caprylate), 1 wt. % of a preservative (e.g., phenoxyethanol and ethylhexylglycerine), fragrance (e.g., Profumo Fiori D'acqua) in an amount of 0.2 wt. %, 0.4 wt. % or 0.7 wt. %, 0.05 wt. % of an antioxidant (e.g., a mixture of tocopherol, lecithin, ascorbyl palmitate and citric acid), and balance solvent (e.g., water), wherein the EPA and GLA are present in a weight-to-weight ratio of about 4:1. In one such embodiment, the EPA and GLA are present in amounts of 0.815 wt. % and 0.285 wt. %, respectively, and the fragrance is present in an amount of 0.2 wt. %. In another such embodiment, the EPA and GLA are present in amounts of 1.631 wt. % and 0.57 wt. %, respectively, and the fragrance is present in an amount of 0.4 wt. %. In yet another such embodiment, the EPA and GLA are present in amounts of 4.08 wt. % and 1.425 wt. %, respectively, and the fragrance is present in an amount of 0.7 wt. %.

In some embodiments, the cosmetic composition comprises or consists of: 0.815 wt. % to 4.08 wt. % of EPA, 0.285 wt. % to 1.425 wt. % of GLA, 0.1 wt. % of a sequestrant (e.g., disodium EDTA), 3 wt. % of a humectant (e.g., glycerine), 0.5 wt. % of a thickening agent (e.g., sodium polyacrylate), 5 wt. % of an emulsifier (e.g., a mixture of glyceryl stearate citrate, glyceryl stearate and behenyl alcohol), 10 wt. % of an emollient (e.g., a mixture of C12-15 alkyl benzoate, cetearyl isononanoate and butyrospermum parkii butter), 1 wt. % of a preservative (e.g., phenoxyethanol and ethylhexylglycerine), 0.7 wt. % of fragrance (e.g., Profumo Fiori D'acqua), 0.02 wt. % of an antioxidant (e.g., a mixture of dimethylmethoxy chromanol and ascorbyl palmitate), 0.3 wt. % of a pH modifier (e.g., sodium hydroxide), 1 wt. % of an adsorbing agent (e.g., aluminum starch octenylsuccinate), and balance solvent (e.g., water), wherein the EPA and GLA are present in a weight-to-weight ratio of about 4:1. In one such embodiment, the EPA and GLA are present in amounts of 0.815 wt. % and 0.285 wt. %. In another such embodiment, the EPA and GLA are present in amounts of 1.631 wt. % and 0.57 wt. %, respectively. In yet another such embodiment, the EPA and GLA are present in amounts of 4.08 wt. % and 1.425 wt. %, respectively. In some embodiments, the cosmetic composition is free of unpleasant odors (e.g., has a cosmetically acceptable odor).

Cosmetic compositions of the present disclosure can be made according to any suitable method known in the art. Typically, the solvents, humectants, and sequestrants are added to a suitably sized main vessel and heated to a temperature of about 70 C. to about 75 C. While heating, thickening agent is added and homogenized at high speed for an effective time, typically about 15 minutes. In a second vessel, the emulsifiers and emollients are melted together (e.g., heated to about 70 C. to about 75 C.), and the melted mixture is added to the main vessel. The main vessel is then homogenized and cooled to about 25 C. If used, the adsorbing agent is next heated in a third vessel to about 50° C. and added to the main vessel. The preservative system is then heated to 35 C. and then added to the main vessel. Next, fragrances and antioxidants are combined and then added to the main vessel. The pH modifier is then added to the main vessel. The EPA and GLA are then combined in a separate vessel before being added to the main vessel.

Cosmetic compositions of the present disclosure may be used as any type of cosmetic product including, for example, topical compositions (e.g., creams, powders, balms, ointments, etc.), lotions, and the like. In some embodiments, the cosmetic composition is a topical formulation.

In some embodiments, a method of treating and/or preventing wrinkles comprises topically administering to skin of a subject an effective amount of a cosmetic composition as disclosed herein. In some embodiments, the cosmetic composition is applied once per day, twice per day, three times per day, four times per day, or more than four times per day. In some embodiments, the cosmetic composition is topically applied for at least one week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 26 weeks, at least 52 weeks, at least 2 years, at least 3 years, at least 4 years, at least 5 years, at least 6 years, at least 7 years, at least 8 years, at least 9 years, or at least 10 years.

EXAMPLES

Example 1

Topical Formulation "A"

A topical composition was prepared by combining the components listed in Table 1 according to the method described above. EPA free fatty acid was provided in the form of a composition comprising 98.1 wt. % EPA free acid GLA free fatty acid was provided in the form of a composition comprising 70.2 wt. % GLA free acid. Values for EPA and GLA reflect the purity of the composition from which each was added. The final formulation had the composition shown in Table 1, below, as follows;

TABLE 1

Composition of Topical Formulation "A"

| Ingredient | Chemical Name | Function | Weight Percent (wt. %) | | |
|---|---|---|---|---|---|
| | | | Low | Medium | High |
| Purified Water | Water | Solvent | 81.590 | 80.289 | 76.685 |
| Trilon B | Disodium EDTA | Sequestrant | 0.100 | 0.100 | 0.100 |
| Glycerine Veg. PH EUR 99.5% | Glcerin | Humectant | 3.000 | 3.000 | 3.000 |
| Silwax WS | PEG-8-Dimethicone | Texturizing Agent | 2.000 | 2.000 | 2.000 |
| Cosmedia SP | Sodium Polyacrylate | Thickening Agent | 1.000 | 1.000 | 1.000 |
| Cetiol Sensoft | Propylheptyl Caprylate | Emollient | 3.000 | 3.000 | 3.000 |
| Gransil EPS | Polysilicone-11 & Laureth 12 | Texturizing Agent | 2.000 | 2.000 | 2.000 |
| Velvesil DM | Dimethicone & Cetearyl Dimethicone Crosspolymer | Texturizing Agent | 2.000 | 2.000 | 2.000 |
| Cosmedia Silc | Silica | Texturizing Agent | 1.500 | 1.500 | 1.500 |
| Granpowder USQ | Polyurethane and Polymethylsilsesquioxane | Texturizing Agent | 1.500 | 1.500 | 1.500 |
| Euxyl PE 9010 | Phenoxyethanol & Ethylhexylglycerin | Preservative | 1.000 | 1.000 | 1.000 |
| Profumo Fiori D'acqua 85328 | | Fragrance | 0.200 | 0.400 | 0.700 |
| Lipochroman | Dimethylmethoxy Chromanol | Antioxidant | 0.010 | 0.010 | 0.010 |
| EPA FFA | Eicosapentaenoic Acid | Active | 0.815 | 1.631 | 4.080 |
| GLA FFA | Gamma Linolenic Acid | Active | 0.285 | 0.570 | 1.425 |

Example 2

Topical Formulation "B"

A topical composition was prepared by combining the components listed in Table 2 according to the method described above. EPA free fatty acid was added in the form of a composition comprising 98.1 wt. % EPA free acid GLA free fatty acid was added in the form of a composition comprising 70.2 wt. % GLA free acid. Values for EPA and GLA reflect the purity of the composition from which each was added. The final formulation had the composition shown in Table 2, below.

Example 3

Topical Formulation "C"

A topical composition was prepared was prepared by combining water, glycerine and disodium EDTA in a main vessel and heating to 70-70 C. While the mixture was heating, the thickening agent (sodium polyacrylate) was added and homogenized at high speed for 15 minutes. In a secondary vessel, the emulsifiers and emollients were combined and heated to 70-75° C. The melted emulsifiers and emollients were then added to the main vessel and homogenized for 15 minutes. The mixture was then cooled to 25 C. The adsorbing agent was heated to 50 C. and added to the main vessel. The

TABLE 2

Composition of Topical Formulation "B"

| Ingredient | Chemical Name | Function | Weight Percent (wt. %) | | |
|---|---|---|---|---|---|
| | | | Low | Medium | High |
| Purified Water | Water | Solvent | 82.550 | 81.249 | 77.645 |
| Trilon B | Disodium EDTA | Sequestrant | 0.100 | 0.100 | 0.100 |
| Glycerine Veg. PH EUR 99.5% | Glycerin | Humectant | 3.000 | 3.000 | 3.000 |
| Silwax WS | PEG-8-Dimethicone | Texturizing Agent | 2.000 | 2.000 | 2.000 |
| Aristoflex AVC | Polymeric Sulphonic Acid | Thickening Agent | 1.000 | 1.000 | 1.000 |
| Cetiol Sensoft | Propylheptyl Caprylate | Emollient | 3.000 | 3.000 | 3.000 |
| Gransil EPS | Polysilicone-11 & Laureth 12 | Texturizing Agent | 2.000 | 2.000 | 2.000 |
| Velvesil DM | Dimethicone & Cetearyl Dimethicone Crosspolymer | Texturizing Agent | 2.000 | 2.000 | 2.000 |
| Cosmedia Silc | Silica | Texturizing Agent | 2.000 | 2.000 | 2.000 |
| Euxyl PE 9010 | Phenoxyethanol & Ethylhexylglycerin | Preservative | 1.000 | 1.000 | 1.000 |
| Profumo Fiori Dacqua 85328 | | Fragrance | 0.200 | 0.400 | 0.700 |
| Aperoxide TLA | Tocopherol, Lecithin, Ascorbyl Palmitate and Citric Acid | Antioxidant | 0.050 | 0.050 | 0.050 |
| EPA FFA | Eicosapentaenoic Acid | Active | 0.815 | 1.631 | 4.080 |
| GLA FFA | Gamma Linolenic Acid | Active | 0.285 | 0.570 | 1.425 | preservative was then heated to 35° C. before being added to the main vessel. The fragrance and antioxidants were combined and then added to the main vessel. The pH modifier was added to the main vessel, followed by a mixture of the EPA and GLA.

The final formulation had the composition shown in Table 3, below.

TABLE 3

Composition of Topical Formula "C"

| Ingredient | Chemical Name | Function | Weight Percent (wt. %) | | |
| --- | --- | --- | --- | --- | --- |
| | | | Low | Medium | High |
| Purified Water | Water | Solvent | 77.280 | 76.179 | 72.875 |
| Trilon B | Disodium EDTA | Sequestrant | 0.100 | 0.100 | 0.100 |
| Glycerine Veg. PH EUR 99.5% | Glycerin | Humectant | 3.000 | 3.000 | 3.000 |
| Cosmedia SP | Sodium Polyacrylate | Thickening Agent | 0.500 | 0.500 | 0.500 |
| Imwitor 372P | Glyceryl Stearate Citrate | Emulsifier | 2.000 | 2.000 | 2.000 |
| Lincol BAS | C12-15 Alkyl Benzoate | Emollient | 3.000 | 3.000 | 3.000 |
| Lincol SN | Cetearyl Isononanoate | Emollient | 5.000 | 5.000 | 5.000 |
| Cutina GMS/Bergabest GS40/Lincol GMS | Glyceryl Stearate | Emulsifier | 2.000 | 2.000 | 2.000 |
| Lanette 22/Vegarol 22/Akest AB/Nafol 1822C | Behenyl Alcohol | Co-Emulsifier | 1.000 | 1.000 | 1.000 |
| Burro Di KARITE | *Butyrospermum Parkii* Butter | Emollient | 2.000 | 2.000 | 2.000 |
| Dry - Flo PC | Aluminum Starch Octenylsuccinate | Adsorbing Agent | 1.000 | 1.000 | 1.000 |
| Euxyl PE 9010 | Phenoxyethanol & Ethylhexylglycerin | Preservative System | 1.000 | 1.000 | 1.000 |
| Profumo Fiori Dacqua 85328 | Fragrance | Odour Masking | 0.700 | 0.700 | 0.700 |
| Lipochroman | Dimethylmethoxy Chromanol | Antioxidant | 0.010 | 0.010 | 0.010 |
| Ascorbyl Palmitate | Ascorbyl Palmitate | Antioxidant | 0.010 | 0.010 | 0.010 |
| Sodium Hydroxide | Sodium Hydroxide | pH Modifier | 0.300 | 0.300 | 0.300 |
| EPA FFA | Eicosapentaenoic Acid | Active | 0.815 | 1.631 | 4.080 |
| GLA FFA | Gamma Linolenic Acid | Active | 0.285 | 0.570 | 1.425 |

Surprisingly, topical formulation C was devoid of the unpleasant odor commonly associated with compositions comprising fatty acids in free acid form.

Example 4

Properties of Formulations A to C

The color, pH, and viscosity (20° C.) of Formulations A to C were determined according to standard methods, as shown in Table 4, below.

TABLE 4

Properties of Formulations A to C.

| Formulation | Low/Medium/High | Color | pH | Viscosity (20° C.) |
| --- | --- | --- | --- | --- |
| A | Low | Off-white | 5.83 | 22,000 mPas |
| | Medium | Off-white | 5.84 | 21,800 mPas |
| | High | Off-white, slightly yellow | 5.81 | 18,000 mPas |
| B | Low | Off-white | 5.35 | 10,200 mPas |
| | Medium | Off-white | 5.32 | 10,300 mPas |
| | High | Off-white, slightly yellow | 5.28 | 11,200 mPas |
| C | Low | Off-white | 7.10 | 33,000 mPas |
| | Medium | Ivory-white | 7.12 | 32,100 mPas |
| | High | Ivory | 7.10 | 30,600 mPas |

Example 5

Antioxidant Capabilities of Disclosed Compositions

A study to determine the antioxidant capabilities of skin after application of Formulations A-C of Examples 1-3 includes 16 male and female subjects, each age 35 to 50 years.

Chromameter measurements are performed on the volar forearm to define each subject's individual typography angle ("ITA°"). Six small spots are then exposed to ITA°-dependent doses of UVA/UVB radiation. After 24 hours, each subject's minimal erythemal dose ("MED") is assessed.

Four test areas are defined on a non-UV-exposed portion of each subject's volar forearm. One test area serves as a negative control, while a composition of each of Formulations A-C of Examples 1-3 is applied to the other three test areas once per day for three days. Two hours after the application on day 3, each test area receives twice the MED dose of UVA/UVB light. After a 24-hour waiting period, chromametric measurements are obtained, and biopsies from each of the three test areas and the negative control area are collected and analyzed.

Analysis of the skin biopsies includes determining the content of at least three markers: matrix metalloproteinase-1 ("MMP-1"), malondialdehyde ("MDA") and interleukin-8 ("IL-8"). Differences between the treated test areas and the negative control are determined using standard statistical methods.

Example 6

Effect of Disclosed Compositions on Biophysical Properties of Skin

A study to determine the effect of Formulations A-C of Examples 1-3 includes 28 male and female subjects, each age 35 to 50 years. Chromameter measurements are performed on the volar forearm to define each subject's individual typography angle ("ITA°"). Six small spots are then exposed to ITA°-dependent doses of UVA/UVB radiation. After 24 hours, each subject's minimal erythemal dose ("MED") is assessed. Baseline biophysical measurements are also obtained at this time, including epidermal thickness (e.g., by a Vivascope or similar instrument), skin elasticity (e.g., by a Cutometer or similar instrument), skin hydration (e.g., by a Corneometer or similar instrument), and skin roughness/fine line assessment/3-dimensional structure (e.g., by use of a Phase-shifted Rapid In vivo Measurement Of human Skin—"PRIMOS"—or a similar instrument).

Each subject then applies each of Formulations A-C of Examples 1-3 twice daily for 12 weeks. During the 12-week test period, each subject visits a test facility to be exposed to suberythemal irradiation by a defined solar simulator.

At the end of the 12-week test period, biophysical measurements as described above are obtained, and skin biopsies are procured. Epidermal thickness, papillary index, and collagen fiber networks are assessed, along with determination of COX-2 and procollagen-1 levels. Differences between the test areas and the negative control are determined using standard statistical methods.

Example 7

Effect of Formulations A to C on Skin Roughness Induced by Suberythemal UV Irradiation A study to determine the efficacy of Formulations A to C to prevent drying out and roughening of the skin during repeated suberythemal irradiation with a sun simulator that emits UVB and UVA radiation is performed. The subjects include fourteen male and female humans each having type II or type III skin.

During the week before treatment, the minimum erythemal dose (MED) for each subject is determined by irradiating six small spots on the subject's volar forearm with a sun simulator (UVASPOT 1000, Hönle). Dose increments are increased by 25% to detect the MED, which is read 16-24 hours after irradiation.

Each subject's volar forearm area is divided into four 4 cm by 5 cm test areas. One area serves as an untreated, irradiated control. A second area is not treated and is not irradiated to serve as a second control.

On days 1 to 12, product applications are performed by the subjects with the exception that applications performed in the morning of the days with an appointment at the study site are performed by trained personnel. On each test area, 2 mg per $cm^2$ of one of Formulations A to C is applied by the trained personnel. The subjects are similarly trained by a technician to apply the same 2 mg per $cm^2$ dose. Fifteen minutes after the Formulation is applied, irradiation on the 3 irradiated test areas is performed with the sun simulator. On days 1 and 3, 0.6 MED are irradiated. On days 5 and 8, 0.75 MED are irradiated, and on days 10 and 12, 1 MED is irradiated. In cases of visible erythema on one or more test areas, the irradiation is skipped for the subject on all test areas until no more erythema is apparent.

Measurements of skin roughness is performed at baseline and on day 12. Measurements are taken before test product application. Using Phase-shifted Rapid In vivo Measurement Of human Skin (PRIMOS), a three-dimensional surface structure of the investigated skin site is captured. The measuring principle is based on digital fringe projection. The fringes that are projected are detected with a CCD camera. The three-dimensional structure is then calculated from the position of the fringes in combination with the gray values of each pixel.

From the captured three-dimensional structure, roughness parameters are calculated. The parameters Rz and Ra are chosen, representing mainly the rough structure (Rz) and the finer skin structure (Ra). An increase or decrease in the roughness parameters corresponded to an increase or decrease in the degree of skin roughness.

Measurements of skin moisture (KAP) are performed at baseline and on days 3, 5, 10 and 12. Measurements are taken before test product application. The evaluation is performed with a Corneometer (CM 825) and is based on the capacitance measuring principle—that is, the distinctly different dielectric constants of water and other substances. This method is described in the literature in detail and is generally accepted as a reproducible and reliable parameter for skin hydration measurements. As standard procedure, measurements are repeated 5 times. Mean values are taken from the 3 middle measuring points; the highest and lowest values are dismissed. By this approach more stable values were achieved.

For all parameters, appropriate statistical methods are used to analyze the differences between the test products and the untreated control.

Example 8

Perceived Odor of Formulations A to C

A study was conducted to determine the perceived odor of the compositions of Formulations A to C as prepared according to Example 1. A small amount of each of the compositions was randomly applied to the back of the hand or wrist of each of four participating subjects. Each subject reported the level of "fishy" odor over several minutes on a Lichert-type scale as shown in Table 5 below.

TABLE 5

Odor Levels of Formulations A to C.

| Formulation | Low | Low (Avg.) | Medium | Medium (Avg.) | High | High (Avg.) |
|---|---|---|---|---|---|---|
| A | +, −, −, + | −/+ | ++, +, +, ++ | +/++ | +++, ++, ++, +++ | ++/+++ |
| B | +, −, −, + | −/+ | ++, +, +, ++ | +/++ | +++, ++, ++, +++ | ++/+++ |
| C | −, −, −, − | − | −, −, −, − | − | +, −, +, + | + |

These study data indicate that the composition of Formulation C surprisingly has a cosmetically acceptable odor (e.g., is free of unpleasant odors), whereas the compositions of Formulation A or Formulation B at the same levels of EPA and GLA free fatty acids.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

What is claimed is:

1. A cosmetic composition comprising eicosapentaenoic free acid; gamma-linolenic free acid; and one or more cosmetically acceptable excipients, wherein the eicosapentaenoic free acid and the gamma-linolenic free acid are present in a weight ratio of about 2:1 to about 8:1, and wherein the eicosapentaenoic free acid is present in an amount up to 8 wt. %.

2. The composition of claim 1, wherein the excipients are selected from the group consisting of: solvents, sequestrants, humectants, thickening agents, emulsifiers, emollients, adsorbing agents, preservatives, fragrances, antioxidants, pH modifiers, texturizing agents, and combinations thereof.

3. The composition of claim 1, wherein the excipients comprise water, disodium EDTA, glycerin, sodium polyacrylate, C12-15 alkyl benzoate, cetearyl isononanoate, butyrospermum parkii butter, dimethylmethoxy chromanol, Ascorbyl palmitate, glyceryl stearate citrate, glyceryl stearate, behenyl alcohol, Sodium hydroxide and aluminum starch octenylsuccinate.

4. The composition of claim 1, wherein the eicosapentaenoic free acid is present in an amount of about 0.8 wt. % to about 4 wt. %.

5. The composition of claim 1, wherein the gamma linolenic free acid is present in an amount of about 0.1 wt. % to about 3 wt. %, about 0.2 wt. % to about 1.5 wt. %, about 0.285 wt. %, about 0.570 wt. %, or about 1.425 wt. %.

6. The composition of claim 1, wherein the eicosapentaenoic free acid is present in an amount of about 0.815 wt. %, and the gamma linolenic acid is present in an amount of about 0.285 wt. %.

7. The composition of claim 1, wherein the eicosapentaenoic free acid is present in an amount of about 1.631 wt. %, and the gamma linolenic acid is present in an amount of about 0.570 wt. %.

8. The composition of claim 1, wherein the eicosapentaenoic free acid is present in an amount of about 4.080 wt. %, and the gamma linolenic acid is present in an amount of about 1.425 wt. %.

9. The composition of claim 1, wherein the eicosapentaenoic free acid is derived from a composition comprising at least 95% by weight eicosapentaenoic free acid.

10. The composition of claim 1, wherein the gamma linolenic free acid is derived from a composition comprising at least 70% by weight gamma linolenic free acid.

11. The composition of claim 1, wherein the eicosapentaenoic free acid is derived from a composition comprising at least 95% by weight eicosapentaenoic free acid and wherein the gamma linolenic free acid is derived from a composition comprising at least 70% by weight gamma linolenic free acid.

12. The composition of claim 1, wherein the gamma linolenic free acid is derived from a composition comprising at least 70% by weight and no more than 90% by weight gamma linolenic free acid.

13. The composition of claim 1, wherein the gamma linolenic free acid is derived from a composition comprising at least 70% by weight gamma linolenic free acid and at least one of the free acids of Palmitic acid, Stearic acid, Oleic acid, Linolenic acid, Icosenoic acid, and Docosenoic acid.

14. The composition of claim 1, wherein the composition comprises about 10 wt. % or about 5 wt. % of all free fatty acids present in the composition.

15. The composition of claim 1, comprising:
about 0.815 wt. % to about 4.08 wt. % of EPA;
about 0.285 wt. % to about 1.425 wt. % of GLA;
about 3.0 wt % of glycerin;
about 0.1 wt. % of disodium EDTA;
about 0.5 wt. % of sodium polyacrylate;
about 2 wt. % of glyceryl stearate citrate;
about 3 wt. % of C12-15 alkyl benzoate;
about 5 wt. % of cetearyl isononanoate;
about 2 wt. % of glyceryl stearate;
about 1 wt. % of behenyl alcohol;
about 2 wt. % of butyrospermum parkii butter;
about 1 wt. % of aluminum starch octenylsuccinate;
about 1 wt. % of phenoxyethanol & ethylhexylglycerin;
about 0.7 wt. % of a fragrance;
about 0.01 wt. % of dimethylmethoxy chromanol;
about 0.1 wt. % of ascorbyl palmitate;
about 0.3 wt. % of sodium hydroxide; and
balance water.

16. The composition of claim 1, wherein the composition has a cosmetically acceptable odor.

17. A method of ameliorating a skin disease or disorder in a subject wherein the skin disease or disorder is selected from the group consisting of wrinkles and seborrheic dermatitis, the method comprising topically administering a composition of claim 1 to at least a portion of the skin of the subject.

18. The method of claim 17, wherein skin disease or disorder is wrinkles.

19. The method of claim 17, wherein skin disease or disorder is seborrheic dermatitis.

* * * * *